United States Patent [19]

Huskey

[11] 4,434,807

[45] Mar. 6, 1984

[54] DENTAL FLOSSING AID

[76] Inventor: Joseph E. Huskey, P.O. Box 476, Copperhill, Tenn. 37317

[21] Appl. No.: 304,116

[22] Filed: Sep. 21, 1981

[51] Int. Cl.³ .............................................. A61C 15/00
[52] U.S. Cl. .................................. 132/92 R; 132/92 A
[58] Field of Search ................... 132/89, 90, 91, 92 R, 132/92 A

[56] References Cited

U.S. PATENT DOCUMENTS

| | | | |
|---|---|---|---|
| 1,465,669 | 8/1923 | Hochstadter | 132/92 A |
| 2,052,520 | 8/1936 | Sonnenberg | 132/92 R |
| 3,881,502 | 5/1975 | Bennington | 132/91 |
| 3,882,879 | 5/1975 | Lucas | 132/92 R |
| 3,885,579 | 5/1975 | Navrat | 132/92 R |
| 3,908,678 | 9/1975 | Conn et al. | 132/92 A |
| 3,913,597 | 10/1975 | Day | 132/92 A |
| 3,924,647 | 12/1975 | Lindblad | 132/92 R |
| 4,094,328 | 6/1978 | Ray | 132/91 |

Primary Examiner—John J. Wilson
Attorney, Agent, or Firm—Louis T. Isaf

[57] ABSTRACT

A dental flossing aid for dispensing and aiding in the use of dental floss for cleaning teeth, comprises an elongated bodymember on which is mounted a supply of dental floss and which comprises a plurality of holes bored through the bodymember. The bodymember is elongated for projecting into the mouth cavity. Dental floss is threaded through the bored holes of the bodymember and extended to the outermost end of the bodymember; the bores serving to develop tension in the dental floss to resist the removal of floss from the floss supply. A pushkey assembly is provided for overcoming the tension and assisting in advancing the dental floss.

7 Claims, 7 Drawing Figures

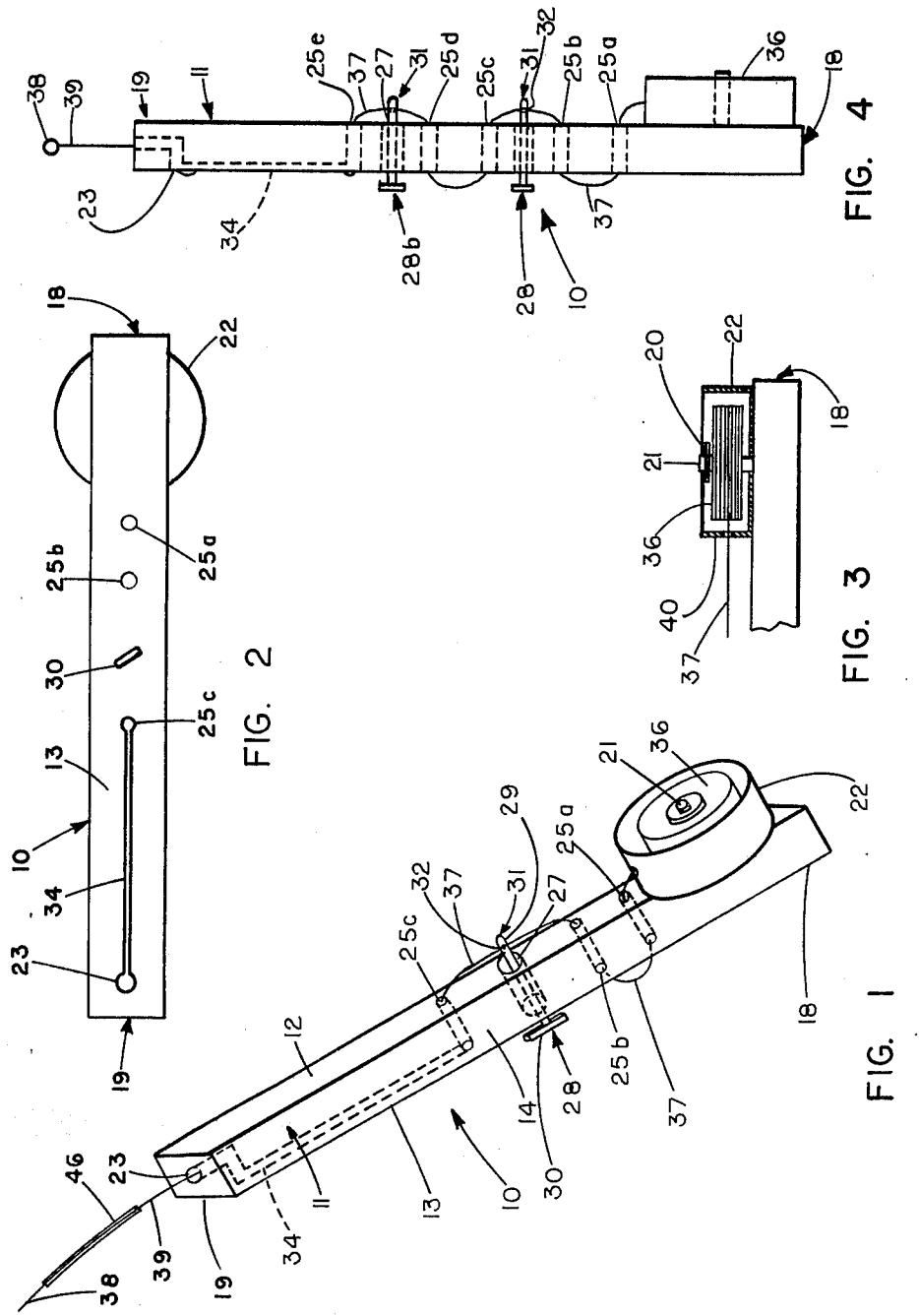

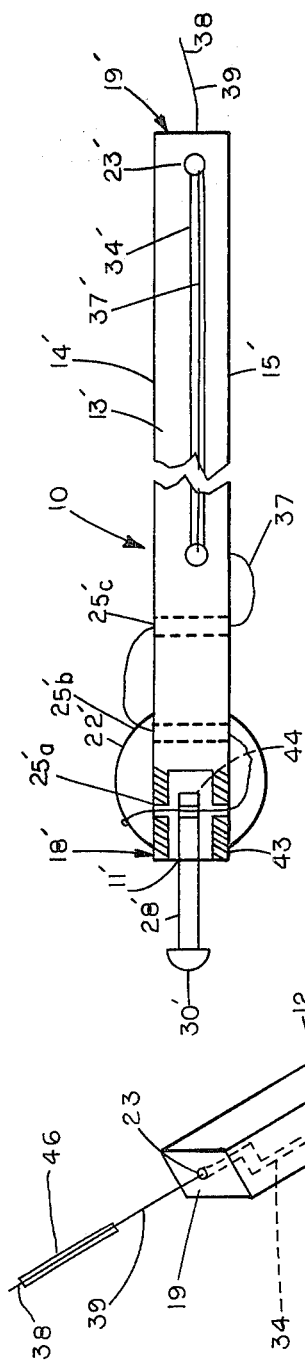
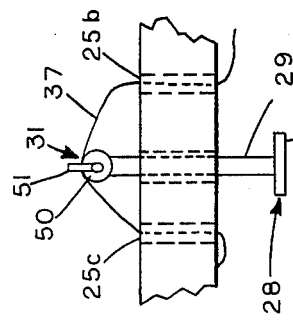
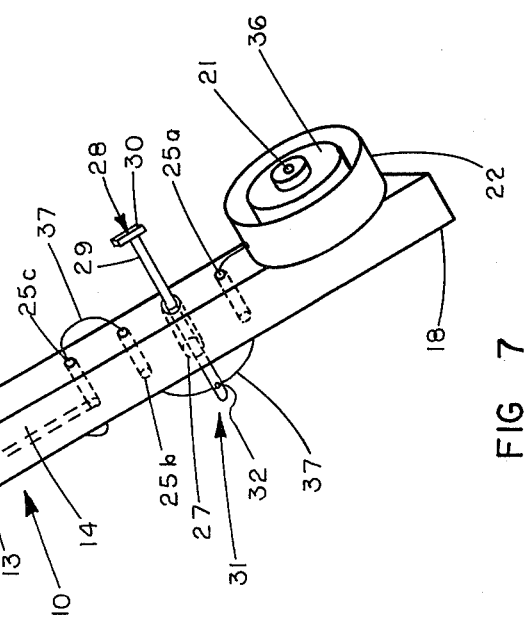
FIG. 5
FIG. 6
FIG. 7

DENTAL FLOSSING AID

FIELD OF THE INVENTION

The present invention relates generally to dental flossing instruments.

BACKGROUND OF THE INVENTION

The use of dental floss is a well known practice for cleaning food particles from the crevices between teeth to aid in the maintenance of good oral hygiene.

Flossing is accomplished by placing a string of dental floss at the crevice between two teeth and moving the string back and forth to work the dental floss up and down through the crevices. Typically, the string of dental floss is held with one end in each hand of the user and the sting is moved about the inside of the mouth by projecting it into the mouth using the index finger of one or both hands. Using the fingers to move the dental floss about within the mouth is somewhat awkward and has led to the development of various devices for the purposes of assisting in the minipulation of the dental floss. Two such dental flossing instruments are shown in U.S. Pat. Nos. 3,882,879 and 3,908,678.

Whenever such flossing instruments are utilized, it is preferable that there be easy, practical means of creating tension in the string of dental floss and also means for providing advancement (lengthening) of the string.

SUMMARY OF THE INVENTION

Briefly described, the present invention consist of a device for dispensing and aiding in the use of dental floss for cleaning teeth. In its presently preferred embodiment, the present invention comprises an elongated body portion similar in size and shape to the body of a tooth brush. At one end of the elongated body is a holder for a roll of dental floss, and a single circular opening is defined at the other end of the body portion. Several holes or bores are defined in the body portion near the floss holder and between the holder and the single circular opening at the other end. A pushkey is movably attached to the body portion in the vicinity of the bores and a groove extends from the bores to the opening at the end of the body portion.

In preparation for use, a roll of floss is placed on the holder. Floss is pulled from the roll, passed through the plurality of bores, along the groove, and through the opening at the end of the body portion, until a few inches are exposed beyond the end. When pulling on the exposed end of the floss, tension is created by the bores to prevent the removal of additional floss from the roll. Pressing on the pushkey pulls additional floss from the roll, overcomes the tension created in the string of floss by the bores, and enables the floss exposed at the end of the body portion to be lengthened.

Therefore, it is an object of the present invention to provide a dental flossing device which is simple in construction and simple to use to floss remote areas of the mouth.

Another object of the present invention is to provide a flossing device which holds dental floss in tension using a minimum of independent and moving components.

Yet another object of the present invention is to provide a flossing device which a user can operate to selectively and simply hold a length of dental floss in tension for flossing a section of teeth and then releasing the tension and advancing the length of floss.

Still another object of the present invention is to provide a simple mechanism for selectively advancing a body in increments along a rope or string, such that the body can slowly descend or "crawl" along the rope.

Other objects, features and advantages of the present invention will become apparent upon reading and understanding this specification when taken in conjunction with the accompanying drawings. dr

BRIEF DESCRIPTION OF THE DRAWINGS

FIG. 1 is a pictorial view of the dental flossing aid in accordance with the present invention.

FIG. 2 is a bottom view (as taken from the left side of FIG. 1) of the invention of FIG. 1, but not showing the string of dental floss.

FIG. 3 is an isolated view of the dental floss mounting end of the present invention of FIG. 1, with a portion broken away for clarity.

FIG. 4 is a side view of the dental flossing aid of the present invention, but showing an alternative view thereof from that of FIG. 1.

FIG. 5 is a bottom view of the dental flossing aid in accordance with the present invention, but showing an alternative embodiment from that in FIG. 1, broken at the center to shorten the view, and broken away to show a sectional view at the dental floss mounting end, for clarity.

FIG. 6 is an isolated view of the dental flossing aid of the present invention, but showing an alternative embodiment from that in FIG. 1.

FIG. 7 is a pictoral view of the dental flossing aid in accordance with the present invention, but showing an alternate embodiment from that in FIG. 1.

DETAILED DESCRIPTION OF THE PREFERRED EMBODIMENT

Referring now with greater detail to the drawings in which like numerals represent like components throughout the several views, FIG. 1 shows a dental flossing aid 10 in accordance with the present invention. The dental flossing aid 10, in its preferred embodiment of FIG. 1, comprises an elongated body portion 11 which body portion has a generally rectangular cross-section. The body portion 11 includes a top side 12, a bottom side 13, a left side 14 and right side 15. The two ends 18, 19 of the body portion 11 shall be termed, respectfully, the floss mounting end 18 and the remote access end or remote end 19.

A post 21 is attached near the floss mounting end 18 of the body portion 11 and extends upwardly from the top side 12 of the body portion. This post 21 is attached in any conventional manner, such as welding or molding as part of the body portion, so as to rigidly attached to the body portion. A cylindrical casing 22 is mounted to the body portion 11 surrounding the post 21. At the remote access end 19 of the body portion 11, a tubular opening 23 is formed through the body portion extending from the bottom side 13 to the outermost end 19 of the body portion, following an approximately "L" shaped path. Along the body portion 11 near, yet removed from the post 21 near the floss mounting end 18, are formed a series of bores 25 extending through the body portion from the top to bottom side thereof. Between two of the bores 25b, 25c is an opening 27 through which a pushkey 28 extends. The pushkey 28 includes a shaft 29 a head 30 and a floss engaging part 31. In the preferred embodiment, the floss engaging part 31 includes an eyelet 32 formed at its extreme outer end. A grooved channel 34 is defined in the body portion 11, cut along the bottom side 13 and extending from the last or outermost bore 25c to the tubular opening 23 (see FIG. 2). As seen in FIG. 1 and more clearly in FIG. 3, a roll of dental floss 36 is mounted on the post 21 within the casing 22. A string of floss 37 passes through an opening 40 in the casing and is threaded along the dental flossing aid 10 as explained below.

Preparation and use of the flossing aid. In preparing the flossing aid for use, a roll of floss 36 is placed on the post 21 at the floss mounting end 18 of the flossing aid 10. Floss is pulled from the roll 36 and the string of floss 37 is passed successively through the bores 25a, 25b, 25c. Between bore 25b and bore 25c, the string 37 is passed through the eyelet 32 of the floss engaging part 31 of pushkey 28. Once the string 37 has passed through the last bore 25c, it is led along the channel 34 and through tubular opening 23. The free end 38 of the string 37 is extended beyond the remote end 19 of the flossing aid 10.

A user grasps the flossing aid 10 about the body portion 11 in one hand. With his other hand, the user grabs the free end 38 of the floss string 37. The user extends the remote end 19 of the flossing aid 10 into his mouth to position the string of dental floss 37 adjacent the teeth and crevices which he desires to clean. The elongated body portion 11 serves as an extension member to assist the user in reaching even the back-most teeth in his mouth without sticking hands or fingers into his mouth. If the exposed length of dental floss 39, that is, that length of floss extending beyond the remote end 19 of the flossing aid 10, is made long enough, the user can floss all of this teeth without placing fingers from either hand into his mouth. A plastic sleeve 46 is provided slidably encircling a portion of the exposed spring length 39. The user holds onto this plastic sleeve when grabbing the free end 38 of string as an aid in gripping the usually thin dental floss 37.

It will be noted, that the path of the dental floss 37 as it passes along the body portion 11 of the flossing aid 10 is somewhat convoluted as a result of being threaded up and down through the bores 25a, 25b, 25c. Although the preferred embodiment of FIG. 1 shows three bores 25a, 25b, 25c, the invention calls for sufficient bores to be formed in order that, once the string 37 has been threaded successively through the bores, there will be sufficient twisting of the sting path such that the length of dental floss cannot easily be extended by pulling on the free end 38 of the string 37. That is, no additional floss can be pulled from the roll 36 by pulling on the free end 38. In this way, the plurality of bores 25 function as a sting tensioning device. The purpose of the string tensioning device is to assist in holding the exposed end of dental floss 39 taut while flossing the teeth.

In order to extend the exposed length 39 of dental floss, a pushkey assembly 28 is provided to overcome the tension within the bores 25 and aid in pulling additional floss 37 from the roll 36. The pushkey 28 functions as a floss advancing device. The pushkey shaft 29 is somewhat longer than the body portion 11 is wide and the shaft slides freely witin the pushkey opening 27. When the string of dental floss 37 is in tension, the string rests against the pushkey floss engaging part 31 forcing the pushkey in a direction toward the bottom 13 of the body portion 11 as seen in FIG. 1. To advance the sting 37, the user pushes on the pushkey head 30 thus moving the shaft 29 in a direction toward the top side 12 of the body portion 11. This pushing action causes the floss engaging part 31 to force the string 37 between bore 25b and bore 25c to move away from the body portion 11. This action, which increases the length of the string path, pulls on the string of dental floss. If the user holds tightly to the free end 38 of the string, so that it cannot be retracted, then additional floss will be pulled from the roll 36. Once additional floss has been pulled from the roll 36, a long loop of string will be left between bores 25b and 25c. The user then pulls on the free end to advance this additional floss along the string path and increase the exposed length 39 of floss. This process of holding the free end 38, pushing on the pushkey head 30, then pulling on the free end 38 can be repeated successively to increase the exposed length of string 39 by increments.

It should be noted that the exact positioning of the pushkey in relation to the bores 25 may vary. Whereas, in the preferred embodiment the pushkey is positioned between the second and third bores 25b, 25c, the exact positioning will depend upon the number of bores through which the string is threaded and, also, on the amount of friction created as the string is pulled through one or more bores 25. Therefore, as seen in FIG. 7, alternate embodiments of the present invention place the pushkey 28 between the first bore 25a and second bore 25b. Of course, in such an arrangement, the pushkey would be turned around such that the head 30 was on the top side 12 of the body portion 11.

FIG. 4 shows an alternative embodiment of the flossing aid 10 in which the convoluted path of the string 37 is made longer by the addition of more bores 25d, 25e. Such an embodiment would be utilized when increased tension would be necessary. Whereas, such added tension would probably not be needed in a dental flossing device, this arrangement may be used on heavier objects in the form of a controlled descent device as discussed in greater detail below. Another embodiment of the dental flossing aid 10 of the present invention is disclosed in FIG. 5. In such an embodiment, the bores 25' are formed in the body portion 11' extending from the left side 14' to the right side 15' of the body portion. The pushkey 28' enters the body portion 11' from the floss mounting end 18'. The pushkey 28' is slidable in and out of a pushkey hole 41 in the embodiment of FIG. 5. The string of dental floss 37 is threaded from the roll (not seen) through the first bore 25a' which first bore intersects with the pushkey hole 41. Pushkey 28' is fitted with an opening 43 at its inner end 44 the string 37 is threaded through the pushkey opening 43 as it passes through bore 25a'.

The string 37, in the embodiment of FIG. 5, is then successively threaded through the remaining bores, along the channel 34' on the bottom side 13' of body portion 11', then through the tubular opening 23' at the remote end 19'. As in the previous embodiments, the plurality of bores 25' serve to convolute the string path thus acting as a tension device to hold the exposed length of dental floss 39 in tension while the user flosses his teeth. The pushkey 28' again functions as a floss advancing device by pulling additional floss from the roll when the pushkey 28' is pushed inward along the pushkey hole 41 to lengthen the string path. The user can thus advance the exposed length of dental floss 39 in the embodiment of FIG. 5 as follows: he pushes the pushkey head 30' with his hand or pushes the head 30' against a stationary object (ie. wall) while holding the string free end 38 to prevent its retraction; he then pulls on the free end 38 of floss and repeats the operation to advance the dental floss in increments.

FIG. 6 shows an isolated view of the push key assembly 28 of an alternative embodiment of the flossing aid 10. The embodiment of FIG. 6 is similar to those embodiments of FIGS. 1 and 4, but the floss engaging part 31 includes a grooved wheel or sheave 50 rotatably mounted to the shaft 29. Forming a loop over the sheave 50 is a string guard 51. While preparing the embodiment of FIG. 6 for use, the string of dental floss 37 is passed through the bore 25b, over the sheave 50 between the sheave and the string guard 51, and then through the bore 25c and along groove 34 as described in other embodiments. In operation, the user pushes on the head 30 of the push key 28 thus extending the sheave 50 upward (as seen in FIG. 6). As the user pulls on the free end 38 of the floss 37, the rotating movement of the sheave 50 lessens normal friction in the string path and permits extended or continuous lengths of floss 37 to be pulled from the roll 36 without alternately pushing and releasing the push key 28.

Whereas the bores 25 are shown in the preferred embodiments as being parallel to one another, the scope of the present invention is not intended to be limited by such parallel relationship. The bores 25 may extend through the body portion 11 at various angles relative to one another so long as they sufficiently convolute the string path so as to create the required tensioning feature.

Control Descent Device

Integral with the present invention is an extended usage of the invented features to function as a controlled descent device. As seen in FIG. 4, the embodiment shown therein, when oriented vertically as seen can be used to lower the body portion 11 down the string in increments by continually extending the exposed length 39 of the string. Such controlled descent device would find usage in lowering from a high building heavy objects suspended from a rope 37 anchored at its free end 38. For example, window cleaners could suspend a platform between two such devices and successively lower the platform from the top of the building to the bottom of the building by increments, stopping when desired to wash windows. With the platform and descent devices 10 suspended from a rope 37 (see FIG. 4), the window cleaner would first push the bottom pushkey 28, thus pulling rope from the rope supply roll 36 to create an added loop of rope between bores 25b and 25c. He would then push pushkey 28b to draw the additional rope from between bores 25b and 25c to create a loop between bores 25d and 25e. The weight of the platform and devices 11 would then cause the additional rope to be pulled through bore 25e, channel 34 and opening 23 to lengthen the exposed length 39 of the rope 37. By repeating the operation, the platform and controlled descent device 11 are lowered downward along the rope 37.

Additional features contemplated as within the scope of this invention are as follows: the grooved channel 34 is replaced by a tubular channel extending along the length of body portion 11, entirely within the body portion; and the body portion 11 is tapered so as to provide a narrow body at the remote end 19; and a floss cutting edge such as those typically found on floss containers is mounted on the body portion for cutting off used portions of the exposed length 39 of floss.

Whereas this invention has been described in detail with particular reference to preferred embodiments thereof, it will be understood that variations and modifications can be effected with spirit and scope of the invention as described hereinbefore as defined in the appended claims.

What is claimed is:

1. A dental flossing device, comprising:
   a floss mounting assembly including means for holding a supply of dental floss;
   an elongated extension member attached to and protruding from said mounting assembly;
   tensioning means associated with said extension member for developing tension in a length of dental floss drawn from the floss supply held at said mounting assembly when the floss is drawn along a floss path from the floss supply through said tensioning means along the length of said extension member toward the outermost end of said extension member, said tensioning means including a plurality of floss accepting bores formed in said extension member and spaced apart from one another along said extension member, each said floss accepting bore extending through said extension member at an angle to the longitudinal axis of the extension member;
   floss advancing means for overcoming the tension of said tensioning means to facilitate withdrawing additional lengths of dental floss from the supply of dental floss held at said floss mounting assembly, said floss advancing means including a first floss engaging member movably mounted on said extension member to engage the length of floss at a point in the floss path between adjacent one of said floss accepting bores, whereby movement of said floss engaging member increases the length of the floss path to be followed by the length of floss.

2. Device of claim 1, wherein said floss advancing means further comprises a second floss engaging member movably mounted on said extension member to engage the length of floss at a second point in the floss path along said extension member.

3. Device of claim 1, wherein said floss engaging member of said floss advancing means includes a rotatable sheave over which a string of dental floss is to be passed.

4. Device of claim 1, wherein said extension member coprises a single-pronged free end being that end opposite said mounting assembly.

5. Device of claim 1, wherein said first flow engaging member is so structured as not to restrict the free movement of floss along the floss path.

6. Device of claim 1, wherein said plurality of floss accepting bores comprises at least three floss accepting bores.

7. Device of claim 6, wherein said first floss engaging member engages a length of floss drawn along the floss path at a point in the floss path which point lies in the floss path at a location so defined that a majority of said floss accepting bores are encountered along the floss path between said point and the outermost end of said extension member.

* * * * *